United States Patent [19]
Fredrickson

[11] Patent Number: 6,001,658
[45] Date of Patent: *Dec. 14, 1999

[54] TEST STRIP APPARATUS AND METHOD FOR DETERMINING PRESENCE OF ANALYTE IN A FLUID SAMPLE

[75] Inventor: Robert A. Fredrickson, Canoe Cove, Canada

[73] Assignee: Diagnostic Chemicals Limited, Charlottetown, Canada

[ * ] Notice: This patent issued on a continued prosecution application filed under 37 CFR 1.53(d), and is subject to the twenty year patent term provisions of 35 U.S.C. 154(a)(2).

[21] Appl. No.: 08/710,259

[22] Filed: Sep. 13, 1996

[51] Int. Cl.$^6$ .................................................. G01N 33/558
[52] U.S. Cl. ............................... 436/514; 422/56; 422/57; 422/58; 422/61; 435/7.9; 435/7.92; 435/7.93; 435/7.94; 435/7.95; 435/287.1; 435/287.2; 435/287.7; 435/805; 435/810; 435/970; 436/169; 436/518; 436/525; 436/531; 436/533; 436/534; 436/805; 436/810
[58] Field of Search .................................. 422/56–58, 61; 435/7.9–7.95, 287.1, 287.2, 287.7, 287.9, 805, 810, 970; 436/514, 518, 525, 531, 533, 534, 169, 805, 810

[56] References Cited

U.S. PATENT DOCUMENTS

| | | |
|---|---|---|
| 3,399,204 | 8/1968 | Frank et al. . |
| 3,399,284 | 8/1968 | Morison et al. . |
| 3,420,205 | 1/1969 | Morison et al. . |
| 3,884,641 | 5/1975 | Kraffczyk et al. . |
| 4,066,646 | 1/1978 | LeBlanc, Jr. et al. . |
| 4,299,916 | 11/1981 | Litman et al. . |
| 4,313,734 | 2/1982 | Leuvering . |
| 4,323,536 | 4/1982 | Columbus . |
| 4,373,932 | 2/1983 | Gribman et al. . |
| 4,376,110 | 3/1983 | David et al. . |
| 4,446,232 | 5/1984 | Liotta . |
| 4,447,192 | 5/1984 | Tuckey . |

(List continued on next page.)

FOREIGN PATENT DOCUMENTS

| | | |
|---|---|---|
| 0 007 654 | 2/1980 | European Pat. Off. . |
| 0 267 006 | 5/1988 | European Pat. Off. . |
| 0 267 066 | 5/1988 | European Pat. Off. . |
| 0 271 204 | 6/1988 | European Pat. Off. . |
| 0 291 194 | 11/1988 | European Pat. Off. . |
| 0 299 428 | 1/1989 | European Pat. Off. . |
| 0 306 772 | 3/1989 | European Pat. Off. . |
| 0 323 605 | 7/1989 | European Pat. Off. . |
| 0 349 215 | 1/1990 | European Pat. Off. . |
| 0 349 295 | 1/1990 | European Pat. Off. . |
| 0 381 173 | 8/1990 | European Pat. Off. . |
| 0 383 619 | 8/1990 | European Pat. Off. . |
| 0 560 411 | 9/1993 | European Pat. Off. . |
| 2 204 398 | 11/1988 | United Kingdom . |
| WO 87/02774 | 5/1987 | WIPO . |
| WO 93/03175 | 2/1993 | WIPO . |
| WO 94/02850 | 2/1994 | WIPO . |

*Primary Examiner*—Christopher L. Chin
*Attorney, Agent, or Firm*—Oliff & Berridge, PLC

[57] ABSTRACT

An apparatus in the form of a test strip is useful for determining the presence of one or more components in a fluid sample. The test strip can be used by itself or in conjunction with an associated housing assembly. The test strip provides a rapid volume, timing and temperature independent visually readable strip for the semi-quantitative detection of a component, such as an analyte.

48 Claims, 1 Drawing Sheet

U.S. PATENT DOCUMENTS

| | | |
|---|---|---|
| 4,533,629 | 8/1985 | Litman et al. . |
| 4,624,929 | 11/1986 | Ullman . |
| 4,770,853 | 9/1988 | Bernstein . |
| 4,774,192 | 9/1988 | Terminiello et al. . |
| 4,806,311 | 2/1989 | Greenquist . |
| 4,857,453 | 8/1989 | Ullman et al. . |
| 4,861,711 | 8/1989 | Friesen et al. . |
| 4,868,108 | 9/1989 | Bahar et al. . |
| 4,877,580 | 10/1989 | Aronowitz et al. . |
| 4,879,215 | 11/1989 | Weng et al. . |
| 4,952,520 | 8/1990 | Okusa et al. . |
| 4,956,275 | 9/1990 | Zuk et al. . |
| 4,956,302 | 9/1990 | Gordon et al. . |
| 4,959,307 | 9/1990 | Olson . |
| 4,960,691 | 10/1990 | Gordon et al. . |
| 4,963,468 | 10/1990 | Olson . |
| 4,965,047 | 10/1990 | Hammond . |
| 4,968,604 | 11/1990 | Beatty . |
| 4,980,298 | 12/1990 | Blake et al. . |
| 4,981,786 | 1/1991 | Dafforn et al. . |
| 4,999,285 | 3/1991 | Stiso . |
| 5,037,764 | 8/1991 | Wilk et al. . |
| 5,073,484 | 12/1991 | Swanson et al. . |
| 5,120,643 | 6/1992 | Ching et al. . |
| 5,135,873 | 8/1992 | Patel et al. . |
| 5,145,789 | 9/1992 | Corti et al. . |
| 5,206,177 | 4/1993 | DeLaCroix et al. . |
| 5,207,984 | 5/1993 | Kheiri . |
| 5,256,372 | 10/1993 | Brooks et al. . |
| 5,260,031 | 11/1993 | Seymour . |
| 5,356,782 | 10/1994 | Moorman et al. . |
| 5,366,902 | 11/1994 | Cox et al. . |
| 5,384,264 | 1/1995 | Chen et al. . |
| 5,500,375 | 3/1996 | Lee-Own et al. . |
| 5,504,013 | 4/1996 | Senior . |
| 5,569,608 | 10/1996 | Sommer . |
| 5,656,502 | 8/1997 | Mackay et al. ............................ 422/58 |

TEST STRIP APPARATUS AND METHOD FOR DETERMINING PRESENCE OF ANALYTE IN A FLUID SAMPLE

BACKGROUND OF THE INVENTION

This invention relates to an apparatus in the form of a test strip, which is useful for determining the presence of one or more components in a fluid sample. The test strip can be used by itself or in conjunction with an associated holding assembly.

The chemical analysis of fluids, including body fluids such as blood, serum, urine and the like; water; fluid food stuffs; etc. is often desirable and frequently necessary. Safety concerns, medical diagnosis, forensics, drug testing and other fields rely on determinations, either qualitative or quantitative, of the components of fluids. These determinations, or assays, must be rapid, reliable and accurate.

A major field of chemical analysis is devoted to "dry chemistry" determination of components and liquid samples. This refers to an apparatus that is dry to the touch. Generally, these apparatus take the form of monolayer and multi-layer test strips and other analytical test elements. These analytical test elements have excellent storage and handling properties, are convenient to use and provide accurate and reliable results.

The determination of a component, for example an analyte, in a fluid sample typically involves reacting the analyte with a binder. The binder undergoes some type of change following the reaction, which leads to a detectable signal. While the change may be caused directly by a reaction with the analyte, the change can also, and usually does, result from some property produced by the interaction between the analyte and the product of the reaction, where the interaction does not exist in unreacted components.

Many types of assays have been developed that utilize the above principles. One important type is the immunoenzymometric assay. This test involves the binding of an analyte of interest with a reaction or binding partner, where the binding partner carries a label. The binding partner is contained in a test strip or other apparatus so that it is non-reactive unless and until its partner analyte contacts the test strip. When this happens, the analyte and labelled binding partner bind to each other, forming a complex. This is accomplished by reacting the label carried by the binding partner with another substance, to form a detectable signal. When the label is an enzyme, as it frequently is, the substance is a substrate for the enzyme. The substrate for the enzyme either forms a visible color or changes color. Measuring the change or amount of color provides a measure of the produced complex, and hence of the analyte.

A problem with the above system is that one must have a sufficient amount of label binding partner to bind essentially all of the analyte in the sample. However, the amount of analyte is generally unknown. Thus, it is necessary to provide excess amounts of labelling binding partner, some of which will not react with the analyte, but carries the label. It nonetheless forms a detectable signal. Thus, unless one separates reacted label carrier from the unreacted portion, no readily perceivable test result can be achieved.

An additional feature of the immunoenzymometric assay is that after the sample has been contacted by the labelled binding partner and some of the partner has been bound to form the complex, the mixture of the complex and unreacted labelled binding partner contacts a sample of solid phase bound analyte or an analyte analog. This analog binds to the uncomplexed labelled binding partner. One can then make a clean division of the labelled partner bound to the analyte and excess labelled binding partner bound to the solid phase. The addition of substrate to either of these gives a color, so a determination can be made.

The immunoenzymometric assay is not the only type of assay used for an analytical system. For example, a competitive assay uses a sample of labelled analyte corresponding to the analyte to be determined, rather than labelled binding partner. A solid phase bound reactant is the binding partner for the analyte and the labelled analyte. If any of the analyte is in the sample that is tested, competition for the binding sites ensues. One then measures the amount of label either in the solid phase or the liquid phase, in the same manner described above for the immunoenzymometric assays, to determine the analyte.

In a displacement assay, a labelled analyte is already bound to a solid phase. When the sample contacts a test strip containing the bound labelled analyte, some of the labelled analyte will be displaced by the binding between the sample analyte and the solid phase bound binding partner.

A sandwich assay is another analytical system for carrying out a chemical analysis. Sandwich assays encompass a broad range of assay types; however, most refer to a formation of a complex between the analyte to be determined, a labelled epitopically active first antibody ($Ab_1 \bullet$, where $\bullet$ indicates that the antibody is a labelled antibody), and a nonlabelled second antibody ($Ab_2$), such as a whole monoclonal second antibody (mAb) or fragment thereof. The sandwich, which forms when the analyte contacts a test strip containing the diffusible second antibody $Ab_2$ and first antibody $Ab_1 \bullet$ is $Ab_2$—An—$Ab_1 \bullet$ The sandwich then contacts a solid phase containing another antibody, which binds to the second antibody, but not to the first antibody. The result of this is separation of the complexed first antibody from the uncomplexed first antibody, which permits a determination in the same manner as discussed above.

SUMMARY OF THE INVENTION

It is an object of the invention to provide an apparatus, in the form of a test strip, for determining one or more components in a fluid sample.

It is a further object of the invention to provide a rapid, volume, timing and temperature independent visually read test strip capable of the semi-quantitative detection of a component, such as an analyte. For example, the test strip can be used for the detection and screening of human urinary albumin (HUA).

Other objects, advantages and salient features of the invention will become apparent from the following detailed description, which, taken in conjunction with the annexed drawings, discloses exemplary embodiments of the invention.

BRIEF DESCRIPTION OF THE FIGURES

The invention will be described in detail with reference to the following drawings in which like reference numerals refer to like elements and wherein.

DETAILED DESCRIPTION OF EMBODIMENTS

Figure 1:
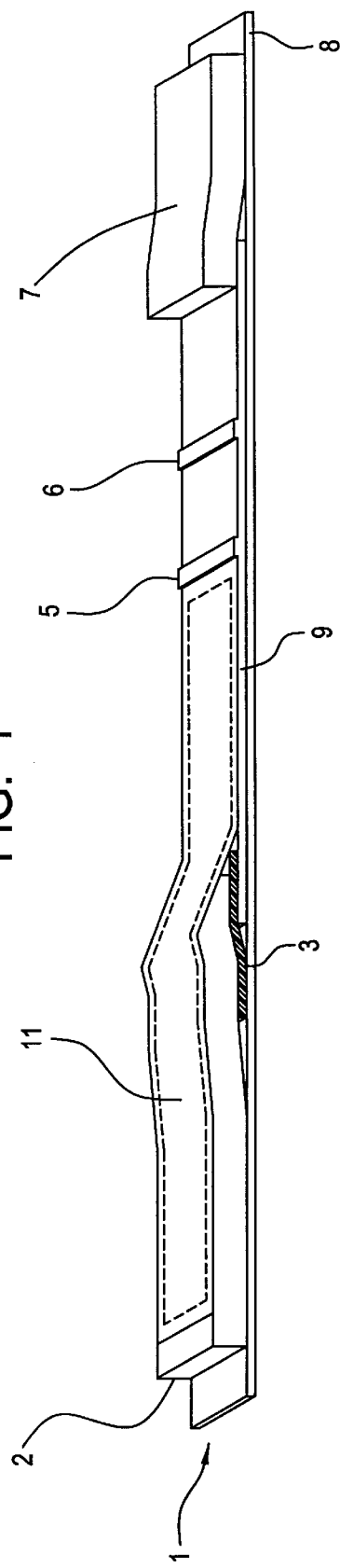
FIG. 1 shows a perspective view of a test strip.
Figure 2:
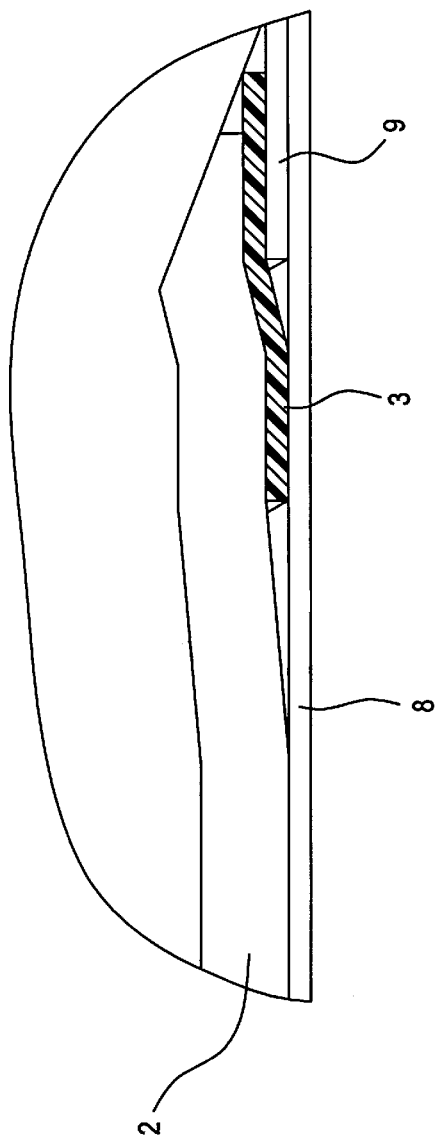
FIG. 2 shows a detailed closeup view of a section of a test strip.

FIG. 1 shows a test strip for the testing of a component in a fluid sample. The test strip may be configured and constructed to test for a variety of different substances in a sample fluid. The following description of the chromatographic test strip assembly will describe the test strip for the semi-quantitative detection of mammalian, e.g., human, albumin in urine using a non-competitive immunometric assay format. However, this is merely exemplary and is not meant to limit the structure or use of the test strip assembly or device in any way.

The chromatographic test strip 1 of FIG. 1 is divided into five regions. These regions include the sample pad 2, the conjugate pad 3, the immobilized analyte zone, stripe or area 5, a control stripe, zone or area 6, and a draw wick pad 7. All the components, including at least the above five zones, may be mounted on a backing such as plastic backing 8, if desired. A membrane 9 is preferably positioned between any backing 8 and at least a portion of the sample pad 2 and conjugate pad 3. The backing 8 is preferably made from a polyvinylchloride (PVC) material. This material is only exemplary and any suitable nonreactive material may be used as the material for backing 8.

The sample pad 2 is positioned on or adjacent one end of the test strip or backing 8. The sample pad 2 can be uncovered. Alternatively, the sample pad can be covered, for example by a plastic tape 11. The cover may be opaque, for example white, and is preferably applied at least over a substantial portion or all of the sample pad 2. The cover may extend up over and cover part or all of the conjugate pad 3 and/or membrane 9. The tape 11 masks the test strip 1 during development and also eliminates confusion regarding the location of the immobilized analyte area 5 and the control area 6, during testing (as described hereinafter). The tape 11 may, in embodiments, be configured to apply pressure to the sample pad 2, thus facilitating the sample fluid's flow through the test strip 1. Further, the tape 11 may be designed and/or applied to protect the test strip 1 during manufacturing.

Furthermore, the tape 11 may protect the test strip 1 during insertion into a holder (not shown) for the test strip 1, such as disclosed in U.S. patent application Ser. No. 08/476,036 to MacKay et al., filed Jun. 7, 1995, whose contents are fully and totally incorporated herein by reference.

The sample pad 2 absorbs the fluid sample, which then migrates by capillary action into the conjugate pad 3. The conjugate pad 3 is impregnated with a diffusible labelled binding partner for the analyte of interest, preferably antibody labelled conjugate, such as antibody labelled with a direct label. Suitable direct labels include, but are not limited to, colloidal gold, colored latex particle, latex microparticle, and the like. The diffusible antibody is a binding partner to the analyte of interest that is known or supposed to be in the test sample. The direct label is preferred as distinguished from an "indirect label," because the direct label is always detectable by itself, e.g., by color. For example, the antibody label can be a cranberry colored colloidal gold or a colored latex particle. No reaction is needed to produce color, as the cranberry colored colloidal gold or other colored direct label in the conjugate pad 3 is already colored. However, the test strip of the present invention can, in embodiments, use an indirect label, with suitable means also being provided to produce the detectable result such as color.

The test strip may include a substance to act as a metering component for metering a concentration of the component of the fluid sample of interest or automatically act to decrease or dilute the concentration of the component of interest in the sample. The substance may be provided in one or more of the sample pad, conjugate pad and/or membrane. Alternatively, the substance may be provided as a separate element, for example, a separate pad. The location of this separate pad can be anywhere along on the test strip before the immobilized analyte area 5 and the control stripe 6. For example, the substance can be an unlabeled antibody or any other appropriate and equivalent substance, which acts to meter or dilute or decrease the concentration of the component of interest in the fluid sample. For example, the metering substance can be an unlabelled antibody that binds with the analyte.

The fluid of the sample being tested migrates into the conjugate pad 3 and dissolves or suspends (e.g., hydrates) the conjugate, which simultaneously facilitates analyte-conjugate binding and migration through the test strip 1. Simultaneously, the sample analyte binds to conjugate as it continues its migration along the test strip 1 towards the immobilized analyte area 5.

The migration then proceeds through the membrane 9. The conjugate pad 3 can overlap the membrane 9. Thus, the fluid sample, analyte-conjugate complex and free analyte and/or conjugate flow or are wicked into the membrane 9 by capillary action.

The conjugate binds to the immobilized analyte (or analyte analog or any other substance that would cross-react with the antibody of interest) at the immobilized analyte area 5 only if it has free binding sites. Conjugate, which has previously been fully bound to the sample analyte, cannot be further bound and therefore passes freely through the immobilized analyte area 5. Conjugate that binds to the immobilized analyte area 5 provides a detectable signal. This detectable signal is inversely related to a concentration of the tested analyte in the fluid sample.

If there is a low level of analyte in the fluid sample, a high level of free conjugate in the migrating fluid results. Therefore, greater amounts of conjugate become immobilized in the immobilized analyte area 5 and color intensity there is relatively high. As the fluid continues to migrate, it will carry more antigen-conjugate complex to the immobilized analyte area 5.

The membrane 9 preferably includes an immobilized analyte and an immobilized antibody. Further, the membrane preferably includes immobilized antibody or other binding particles for the antibody-label conjugate in control area 6. The immobilized antibody may also bind to the conjugate and immobilize both antigen-conjugate and free conjugate. A finite quantitative amount of conjugate distributes itself between these areas 5 and 6, depending on the sample analyte level, producing a color pattern that is distinctly indicative of sample analyte levels in the fluid sample.

The fluid sample continues to migrate along the membrane 9 to the draw wick pad 7, until the draw wick pad 7 is saturated. Once the draw wick pad 7 is saturated, the fluid migration by capillary flow automatically stops. This results in an end point to strip development and testing. No further migration occurs within the test strip 1 due to the saturated state of the draw wick pad 7 and the detection pattern remains stable. The test results are not altered by any further fluid migration because further migration and thus further interaction at the areas 5 and 6 is prevented.

The operation of a test strip in the context of semi-quantitative detection and screening of human urinary albumin will now be described.

The test strip 1 is dipped into a test sample of urine and left to develop. The test strip 1 may be held in a test strip housing, as disclosed in U.S. patent application Ser. No. 08/476,036. Urine wets the sample pad 2 and migrates up the test strip 1 by capillary action. The strip development begins as urine migrates, saturating the sample pad 2 and flowing into the conjugate pad 3. This causes the conjugate, for example colloidal gold or colored latex particles, however any appropriate and equivalent conjugate may be used, contained therein to migrate into the membrane area 9 and the immobilized analyte area 5 and the control area 6.

As seen in FIG. 1, the immobilized analyte area 5 and the control area 6 may be formed as two thin stripes on the membrane 9. The first stripe at the immobilized analyte area 5 encountered by the conjugate is, for example, a band of immobilized human serum albumin (HSA). The second thin stripe at the control area 6, slightly further along the membrane 9 in the direction of fluid flow, is, for example, an immobilized anti-mouse antibody. At the distal end of the test strip 1 is a draw wick pad 8, which facilitates the continuous draw of urine up the strip by capillary action.

While the construction of the immobilized analyte area 5 and the control area 6 are described as stripes, this is only exemplary. Any appropriate size, configuration and/or shape of the immobilized analyte area 5 and the control area 6 are contemplated by this invention. Further, while the conjugate is disclosed as labelled with a direct label of a colloidal gold or a colored latex particle, the immobilized analyte area 5 is disclosed as having HSA and the control area 6 is disclosed as having immobilized anti-mouse antibody, these are also only exemplary. Any appropriate conjugates, binders and the like may be used for testing of different components, and could be selected without undue experimentation by one of ordinary skill in the art.

The interaction of the sample fluid, urine, and the immobilized analyte area 5 and the control area 6 are now described. As noted above, when the sample pad 2 is wetted with a test sample of urine, the urine migrates up the strip, rehydrating the conjugate and facilitating its migration with sample HUA. During migration up the test strip 1, conjugate and HUA react immunochemically. This results in saturated and unsaturated binding sites in the conjugate. The saturated conjugate's binding sites will be sufficiently loaded with sample HUA to preclude binding to immobilized HSA of the immobilized analyte area 5, by the kinetics imposed by the migration rate of the membrane 9. The unsaturated conjugate's binding sites may be sufficiently vacant so that binding of the HUA occurs during subsequent migration. In the absence of HUA, it is preferable that approximately 80–99%, more preferably 90–99%, more preferably about 95% of the conjugate binds to the immobilized analyte area 5 of immobilized HSA, and that remaining conjugate binds to the immobilized antibody control area 6. This produces a sharp line of color at the immobilized analyte zone 5, and a faint band in the immobilized antibody control zone 6.

If the sample has a sufficient amount of HUA, the conjugate may be differently sequestered. Some of the conjugate binds to the HSA at the immobilized analyte area 5 and the remainder of the conjugate further migrates up the strip to the immobilized anti-mouse antibody at the control area 6.

Thus, the principal read area would be the immobilized analyte area 5. The color becomes less intense with increasing sample HUA concentration. Correspondingly, there is an increase in color intensity in the control area 6. The control area 6 indicates the performance of the testing. If neither the immobilized analyte area 5 nor the control area 6 shows color, either the test is not yet complete or the test sample was not applied in sufficient quantity. Color in the control area 6 signifies that the test is complete and that the test strip 1 has functioned correctly, at least from a hydrodynamic view.

The HSA concentration is determined by a reading of the immobilized analyte area 5 and the control area 6 on the membrane 9. The comparison of color intensities in the immobilized analyte area 5 and control area 6 permits a determination concerning the test sample fluid to be made. These two areas form the total detection area. A sample is measured by comparing its color intensity pattern on the test strip 1 with a calibration card (not shown), which shows responses at predetermined concentrations. The card is preferably a high contrast, detailed reproduction of actual dose response profiles to achieve semi-quantitative results.

The assay time for test strip development is generally approximately 0 to 10 minutes, preferably 0–4 minutes and in embodiments 3–4 minutes. The test strip 1, if enclosed within a plastic housing (not shown), can be used in a dip stick format. The housing, as described in U.S. Pat. No. 5,565,502, provides a structure for limiting the amount of fluid contact with the sample pad 3, further insuring a reliable test result. The immobilized analyte area 5 and the control area 6 can be visible through one or more transparent windows or openings in the housing.

The following table illustrates possible results using the test strip 1:

| Immobilized Analyte Area 5 | Control Area 6 | Interpretation |
| --- | --- | --- |
| No color | No color | Strip failure or not used |
| Color | No color | Strip failure/Short sample |
| 95–50% color | 5–50% color | Negative result |
| 49–5% or less color | 51–95% or greater color | Positive result |
| No color | 100% color | Positive result |

The membrane 9 is preferably a nitrocellulose membrane specifically designed for lateral flow. The pore size in an example of such a membrane is approximately 15 µm. The membrane may have a backing, and the membrane with its backing can be laminated on a plastic backing 8. For example, the membrane strip could be a "high flow" nitrocellulose membrane from Millipore, Inc. However, any appropriate material and/or pore size can be used for the membrane.

In embodiments, the conjugate label can be a colloidal gold having gold particles of 20–25 nm mean diameter spherically shaped and cranberry colored. In other embodiments, the conjugate label can be a colored latex particle, having a mean particle diameter of from 50 to 800 nm, preferably from 200 to 400 nm. However, any appropriate material can be used for the conjugate label.

While the invention has been described with respect to examples of specific test sample, label, conjugate, immobilized analyte and immobilized antibody analyte, the invention is not limited thereto. For example, as described in U.S. Pat. No. 4,956,275; European Patent Application 0 267 066; European Patent Application 0 381 173; U.S. Pat. Nos. 4,959,307; 4,960,691; 4,968,604; 4,952,520; PCT 87/02774; U.S. Pat. Nos. 4,963,468; 4,981,786; European Patent Application 0 383 619; U.S. Pat. Nos. 4,313,734; 4,373,932; 4,956,302; 4,624,929; 3,884,641; 4,965,047; 4,770,853; 5,256,372; 4,857,453; 5,145,789; 4,980,298; 3,399,204; 3,420,205; 4,066,646; 5,120,643; 4,447,192; European Patent Application 0 349 295; European Patent Application 0 306 772; European Patent Application 0 299 428; PCT Application 93/03175; European Patent Application 0 291 194; European Patent Application 0 271 204; and European Patent Application 0 323 605, the test strip may be configured in any appropriate fashion, for any appropriate test, to include alternatives of any one or more of the above-described variants. A detailed discussion of these many variants for suitable test strips appears in the above listed documents, the entire contents of which are hereby fully incorporated by reference.

While this invention has been described in conjunction with specific embodiments thereof, it is evident that many alternatives, modifications and variations will be apparent to those skilled in the art. Accordingly, the preferred embodiments of the invention as set forth herein are intended to be illustrative, not limiting. Various changes may be made without departing from the spirit and scope of the invention as defined above.

What is claimed is:

1. A semiquantitative method for determining the presence of an analyte in a sample fluid, comprising
    exposing a portion of a test strip apparatus to said sample fluid to be tested, wherein said test strip apparatus comprises:
        a conjugate pad comprising a diffusible labelled first binding partner that binds with said analyte;
        a first area comprising an immobilized second binding partner that competes with said analyte to bind with said diffusible labelled first binding partner; and
        a second area comprising an immobilized third binding partner that binds with said diffusible labelled first binding partner,
        located in sequence in a capillary fluid flow direction in said test strip apparatus;
    allowing said analyte in said sample fluid to migrate up the test strip apparatus by capillary action; and
    reading a result of said test strip by comparing relative label intensities in said first area and said second area,
    wherein a greater relative label intensity in said second area as compared to said first area indicates the presence of said analyte in said sample fluid in an amount greater than a value determined by the amounts of said first and second binding partners and a lesser relative intensity in said second area as compared to said first area indicates the presence of said analyte in said sample fluid in an amount less than a value determined by the amounts of said first and second binding partners.

2. A method according to claim 1, wherein in an absence of said analyte in said sample fluid, at least 80% of said diffusible labelled first binding partner binds to said immobilized second binding partner.

3. A method according to claim 1, wherein said diffusible labelled first binding partner comprises an antibody-latex microparticle conjugate, said immobilized second binding partner comprises human serum albumin, said immobilized third binding partner comprises an anti-mouse antibody capable of binding with said antibody-latex microparticle conjugate, and said analyte is human urine albumin.

4. A method according to claim 1, wherein said test strip apparatus further comprises a sample pad located upstream of said diffusible labelled first binding partner in said capillary fluid flow direction, and a draw wick pad located downstream of said immobilized third binding partner in said capillary fluid flow direction in said test strip apparatus.

5. A method according to claim 1, wherein said immobilized second binding partner is selected from the group consisting of immobilized analyte and immobilized analyte analog.

6. A method according to claim 1, wherein in an absence of said analyte in said sample fluid, at least 95% of said diffusible labelled first binding partner binds to said immobilized second binding partner.

7. A method according to claim 1, wherein said diffusible labelled first binding partner comprises an antibody-colloidal gold conjugate.

8. A method according to claim 1, wherein said diffusible labelled first binding partner is an antibody-label conjugate.

9. A method according to claim 1, wherein said diffusible labelled first binding partner comprises a visible label.

10. A method according to claim 9, wherein said visible label comprises latex microparticles.

11. A method according to claim 1, wherein said immobilized third binding partner comprises an antibody.

12. A method according to claim 1, wherein said test strip apparatus further comprises a metering component directed against said analyte to sequester a portion of said analyte to meter a concentration of said analyte in said sample fluid, wherein said metering component is located in said test strip apparatus upstream of said immobilized second binding partner in said capillary fluid flow direction.

13. A method according to claim 12, wherein said metering component is an unlabelled antibody.

14. The method of claim 1, wherein said first area comprises sufficient immobilized second binding partner to bind 80–99% of said labelled first binding partner in an absence of said analyte in said sample fluid.

15. The method of claim 1, wherein said first area comprises sufficient immobilized second binding partner to bind 90–99% of said labelled first binding partner in an absence of said analyte in said sample fluid.

16. The method of claim 1, wherein said first area comprises sufficient immobilized second binding partner to bind about 95% of said labelled first binding partner in an absence of said analyte in said sample fluid.

17. A test strip apparatus for semiquantitative determination of an analyte in a sample fluid, comprising
    a sample pad;
    a conjugate pad comprising a diffusible labelled first binding partner that binds with said analyte;
    a first area comprising an immobilized second binding partner that competes with said analyte to bind with said diffusible labelled first binding partner, wherein there is a sufficient amount of said second binding partner to bind at least 80%, but no more than 99%, of said labelled first binding partner in an absence of said analyte in said sample fluid;
    a second area comprising an immobilized third binding partner that binds with said diffusible labelled first binding partner; and
    a draw wick pad,
    located in sequence in a capillary fluid flow direction in said test strip apparatus,
    wherein when said test strip is exposed to said sample fluid, a greater relative label intensity in said second area as compared to said first area indicates the presence of said analyte in said sample fluid in an amount greater than a value determined by the amounts of said first and second binding partners and a lesser relative intensity in said second area as compared to said first area indicates the presence of said analyte in said sample fluid in an amount less than a value determined by the amounts of said first and second binding partners.

18. A test strip apparatus according to claim 17, wherein said diffusible labelled first binding partner comprises an antibody-latex microparticle conjugate, said immobilized second binding partner comprises human serum albumin, and said immobilized third binding partner comprises an anti-mouse antibody capable of binding with said antibody-latex microparticle conjugate.

19. The apparatus of claim 17, wherein there is a sufficient amount of said second binding partner to bind 90–99% of said first binding partner in an absence of said analyte in said sample fluid.

20. The apparatus of claim 17, wherein there is a sufficient amount of said second binding partner to bind about 95% of said first binding partner in an absence of said analyte in said sample fluid.

21. The apparatus of claim 17, wherein said immobilized second binding partner is selected from the group consisting of immobilized analyte and immobilized analyte analog.

22. A semiquantitative method for determining the presence of an analyte in a sample fluid, comprising exposing a portion of a test strip apparatus to said sample fluid to be tested, wherein said test strip apparatus comprises:

a conjugate pad comprising a diffusible labelled first binding partner that binds with said analyte;

a first area comprising an immobilized second binding partner that binds with analyte which has bound to said diffusible labelled first binding partner to form an analyte sandwich, but does not bind with said diffusible labelled first binding partner; and a second area comprising an immobilized third binding partner that binds with said diffusible labelled first binding partner, located in sequence in a capillary fluid flow direction in said test strip apparatus;

allowing said analyte in said sample fluid to migrate up the test strip apparatus by capillary action; and reading a result of said test strip by comparing relative label intensities in said first area and said second area, wherein a greater relative label intensity in said first area as compared to said second area indicates the presence of said analyte in said sample fluid in an amount greater than a value determined by the amounts of said first, second and third binding partners and a lesser relative label intensity in said first area as compared to said second area indicates the presence of said an analyte in said sample fluid in an amount less than a value determined by the amounts of said first, second and third binding partners.

23. The method of claim 22, wherein said immobilized second binding partner is selected from the group consisting of immobilized antibody to said analyte and an antibody recognizing a different epitope on said analyte than the epitope recognized by said labelled first binding partner.

24. A semiquantitative method for determining the presence of an analyte in a sample fluid, comprising exposing a portion of a test strip apparatus to said sample fluid to be tested, wherein said test strip apparatus comprises:

a conjugate pad comprising a diffusible labelled form of said analyte;

a first area comprising an immobilized first binding partner that binds with said analyte and said labelled form of said analyte; and a second area comprising an immobilized second binding partner that binds with any of said analyte not bound to said immobilized first binding partner, located in sequence in a capillary fluid flow direction in said test strip apparatus;

allowing said analyte in said sample fluid to migrate up the test strip apparatus by capillary action; and reading a result of said test strip by comparing relative label intensities in said first area and said second area, wherein a greater relative label intensity in said second area as compared to said first area indicates the presence of said analyte in said sample fluid in an amount greater than a value determined by the amount of said first binding partner and a lesser relative label intensity in said second area as compared to said first area indicates the presence of said analyte in said sample fluid in an amount less than a value determined by the amount of said first binding partner.

25. The method of claim 24, wherein said first area comprises sufficient immobilized first binding partner to bind 80–99% of said labelled analyte in an absence of said analyte in said sample fluid.

26. The method of claim 24, wherein said first area comprises sufficient immobilized first binding partner to bind 90–99% of said labelled analyte in an absence of said analyte in said sample fluid.

27. The method of claim 24, wherein said first area comprises sufficient immobilized first binding partner to bind about 95% of said labelled analyte in an absence of said analyte in said sample fluid.

28. The method of claim 24, wherein said immobilized first binding partner is selected from the group consisting of immobilized polyclonal antibody against said analyte and monoclonal antibody against said analyte.

29. A test strip apparatus for determining the presence of an analyte in a sample fluid, comprising a sample pad;

a conjugate pad comprising a diffusible labelled first binding partner that binds with said analyte;

a metering component;

a first area comprising an immobilized second binding partner that competes with said analyte to bind with said diffusible labelled first binding partner;

a second area comprising an immobilized third binding partner that binds with said diffusible labelled first binding partner; and a draw wick pad, located in sequence in a capillary fluid flow direction in said test strip apparatus.

30. The apparatus of claim 29, wherein in an absence of said analyte in said sample fluid, at least 80% of said diffusible labelled first binding partner binds to said immobilized second binding partner in an absence of said analyte in said sample fluid.

31. The apparatus of claim 29, wherein said diffusible labelled first binding partner comprises an antibody-latex microparticle conjugate, said immobilized second binding partner comprises human serum albumin, said immobilized third binding partner comprises an anti-mouse antibody capable of binding with said antibody-latex microparticle conjugate, and said analyte is human urine albumin.

32. The apparatus of claim 29, wherein said immobilized second binding partner is selected from the group consisting of immobilized analyte and immobilized analyte analog.

33. The apparatus of claim 29, wherein in an absence of said analyte in said sample fluid, at least 95% of said diffusible labelled first binding partner binds to said immobilized second binding partner in an absence of said analyte in said sample fluid.

34. The apparatus of claim 29, wherein said diffusible labelled first binding partner comprises an antibody-colloidal gold conjugate.

35. The apparatus of claim 29, wherein said diffusible labelled first binding partner is an antibody-label conjugate.

36. The apparatus of claim 29, wherein said diffusible labelled first binding partner comprises a visible label.

37. The apparatus of claim 36, wherein said visible label comprises latex microparticles.

38. The apparatus of claim 29, wherein said immobilized third binding partner comprises an antibody.

39. The apparatus of claim 29, wherein said metering component is directed against said analyte to sequester a portion of said analyte to meter a concentration of said analyte in said sample fluid.

40. The apparatus of claim 39, wherein said metering component is an unlabelled antibody.

41. The apparatus of claim 29, wherein said metering component is contained in said conjugate pad.

42. The apparatus of claim 29, wherein said metering component is contained in said sample pad.

43. The apparatus of claim 29, wherein said metering component is contained in a metering pad located prior to said first area in said capillary fluid flow direction.

44. A semiquantitative method for determining the presence of an analyte in a sample fluid, comprising exposing a portion of a test strip apparatus to said sample fluid to be tested, wherein said test strip apparatus comprises:
a conjugate pad comprising a diffusible labelled first binding partner that binds with said analyte;
a metering component;
a first area comprising an immobilized second binding partner that competes with said analyte to bind with said diffusible labelled first binding partner; and
a second area comprising an immobilized third binding partner that binds with said diffusible labelled first binding partner,
located in sequence in a capillary fluid flow direction in said test strip apparatus;

allowing said analyte in said sample fluid to migrate up the test strip apparatus by capillary action; and reading a result of said test strip by comparing relative label intensities in said first area and said second area, wherein a greater relative label intensity in said second area as compared to said first area indicates the presence of said analyte in said sample fluid in an amount greater than a value determined by the amounts of said first and second binding partners and said metering component and a lesser relative label intensity in said second area as compared to said first area indicates the presence of said analyte in said sample fluid in an amount less than a value determined by the amounts of said first and second binding partners and said metering component.

45. The method of claim 44, wherein said immobilized second binding partner is selected from the group consisting of immobilized analyte and immobilized analyte analog.

46. The method of claim 44, wherein said metering component is contained in said conjugate pad.

47. The method of claim 44, wherein said metering component is contained in said sample pad.

48. The method of claim 44, wherein said metering component is contained in a metering pad located prior to said first area in said capillary fluid flow direction.

* * * * *